(12) United States Patent
Sasaki et al.

(10) Patent No.: US 7,645,457 B2
(45) Date of Patent: *Jan. 12, 2010

(54) EMULSIFIED COSMETICS

(75) Inventors: Yuki Sasaki, Minamiashigara (JP); Yasuo Matsumura, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 370 days.

This patent is subject to a terminal disclaimer.

(21) Appl. No.: 10/241,549

(22) Filed: Sep. 12, 2002

(65) Prior Publication Data

US 2003/0180336 A1 Sep. 25, 2003

(30) Foreign Application Priority Data

Mar. 14, 2002 (JP) ............... 2002-070881

(51) Int. Cl.
*A61K 8/02* (2006.01)
(52) U.S. Cl. ...................... 424/401; 427/195
(58) Field of Classification Search ................ 424/400, 424/401, 501, 78.03
See application file for complete search history.

(56) References Cited

U.S. PATENT DOCUMENTS 5,637,291 A 6/1997 Bara et al.
6,080,430 A * 6/2000 Ogawa et al. ............... 424/490
6,207,175 B1 3/2001 Lebreton
2001/0053492 A1 12/2001 Suwabe et al.

FOREIGN PATENT DOCUMENTS

| | | |
|---|---|---|
| CN | 1145217 | 3/1997 |
| CN | 1234407 | 11/1999 |
| CN | 1260165 | 7/2000 |
| EP | 0 942 014 A2 | 9/1999 |
| JP | 57098205 A * | 6/1982 |
| JP | 600184004 A * | 9/1985 |
| JP | 6-122613 | 5/1994 |
| JP | 10059825 A * | 3/1998 |
| JP | A 10-338616 | 12/1998 |
| JP | A 11-130617 | 5/1999 |
| JP | A-2000-267334 | 9/2000 |
| JP | A 2001-151640 | 6/2001 |
| JP | A 2003-55153 | 2/2003 |

* cited by examiner

*Primary Examiner*—Sreeni Padmanabhan
*Assistant Examiner*—Layla Soroush
(74) *Attorney, Agent, or Firm*—Oliff & Berridge, PLC

(57) ABSTRACT

An emulsified cosmetic offering superior sensation of use and r stability comprises 0.1 to 25 wt % of aqueous moisturizing components, 2 to 80 wt % of oil solution components, and 0.1 to 30 wt % of spherical resin particles having hydrophilic groups on their surfaces and an average volume particle size of 2.0 μm to 20.0 μm. The spherical resin particles are made by applying alkali cleaning or acid cleaning to aggregation particles after resin polymerization, and the volume particle size distribution GSDv of the spherical resin particles is 1.3 or less, and the shape factor SF1 thereof is 100 to 140.

16 Claims, No Drawings

EMULSIFIED COSMETICS

BACKGROUND OF THE INVENTION

1. Field of the Invention

The present invention relates to emulsified cosmetics comprising blended therein resin particles which have a spherical, flat, and smooth surface and a uniform particle size, and which create a smooth and uniform spread and an "unsticky" feeling.

2. Description of the Related Art

In general, a cosmetic in which oil phase components such as oils or waxes are emulsified with aqueous phase components using an surfactant (emulsifier) is referred to as an emulsified cosmetic. An emulsified cosmetic has higher durability on a skin surface than does a fine particle cosmetics, provides a moist feel, and has superior dispersibility of fine particles, thus enabling wide-ranged applications including, for example, creams or foundations.

Because a typical emulsified cosmetic is constituted by emulsifying the aqueous phase components with the oil phase components as described above, it is necessary that these components retain a stable emulsification state. Recently, it has become common for spherical resin particles to blended in to improve the tactile feel of the cosmetic. Many of these spherical resin particles are easily uniformly dispersed into the oil phase, but lack an affinity for the aqueous phase, therefore, it is essential to prevent detachment, aggregation, alteration, and the like from occurring. For this problem, it is common to apply methods of blending an emulsion stabilizer, the surfactant, and the like.

A disadvantage of such emulsified cosmetics is their sticky sensation, giving a feeling of thick spread because of poor spreadability during application. Especially when the spreadability during application is poor, an applied cosmetic layer becomes thick or uneven, which is likely to create an unnatural impression. Further, in a recent trend, there has been an increasing desire for cosmetics that provide a natural finish. A natural finish is commonly accomplished by forming a thin and uniform cosmetic-applied layer on the skin. Lately, methods of blending talc powder or spherical polyalkylene resins (Japanese Patent Publication Laid-open No. 11-130617) into the cosmetics are adopted to remove stickiness and improve smooth spread during application.

The spherical resin is typically subjected to surface treatment such as oil solution treatment, silicone compound treatment, fluorine compound treatment, metallic soap treatment, surfactant treatment, amino acid compound treatment or water-soluble polymer treatment, generally in order to add functional characteristics such as water repellency or oil repellency. However, these treatments effect the sensation after application, and not to improving dispersibility. Recent studies have resulted in particles having a strong affinity for the oil phase and aqueous phase because of presence of an organic group bonded directly to part of silicon in silica fine particles and through having a hydroxyl group in part of silicon (Japanese Patent Publication Laid-open No. 2001-151640). However, further improvement in tactile feelings such as an adhesive feeling and smoothness during application, and in reducing the high manufacturing costs of seed polymerization, remain an unfulfilled desire.

According to available studies, the spreadability of cosmetics depends upon physico-chemical properties such as particle shape, particle size distribution, surface conditions, and hardness of these blended spherical particles, and the characteristics of the cosmetics are greatly dependent upon physico-chemical properties such as a glass transition point and average molecular weight, and upon monomers constituting the resin and a weight ratio. Further, cosmetic durability required in the cosmetics is greatly affected by a resin acid value, percentage of moisture content of compounds, water resistance based on the content of impurities and oil resistance.

The conventional spherical particles blended into the emulsified cosmetics were most commonly spherical resin particles prepared by an emulsification polymerization method, a general purpose suspension polymerization method or a precipitation polymerization method, or talc powder. However, because the particle size distribution of the spherical particles prepared using these methods is wide and the surface conditions of the particles are not controlled, there has been a desire for development of cosmetics superior in spreadability of cosmetics when applied and in forming a uniform cosmetic layer.

There has been an especially strong desire for development of emulsified cosmetics in which the spherical resin particles have an affinity not only for the oil phase but also for the aqueous phase, and which demonstrate superior stability.

SUMMARY OF THE INVENTION

In view of the foregoing circumstances, the present inventors have developed as a result of extensive research the present invention after finding out that, by having a very narrow particle size distribution and by blending resin particles having hydrophilic groups on their surfaces, stickiness after application can be controlled, superior spreadability is demonstrated, and, moreover, stability is improved.

Therefore, the present inventors have made it possible to solve the problems mentioned above by adopting the following constitutions:

(1) An emulsified cosmetic, comprising 0.1 to 25 wt % of aqueous moisturizing components; 2 to 80 wt % of oil solution components; and 0.1 to 30 wt % of spherical resin particles having hydrophilic groups on their surfaces and an average volume particle size of 2.0 μm to 20.0 μm.

(2) The emulsified cosmetic according to (1), wherein the spherical resin particles are made by applying alkali cleaning or acid cleaning to aggregation particles after resin polymerization.

(3) The emulsified cosmetic according to (1) or (2), wherein a volume particle size distribution GSDv of the spherical resin particles is 1.3 or less, and a shape factor SF1 thereof is 100 to 140.

(4) The emulsified cosmetic according to any of (1), (2) or (3), wherein a superficial index value of the spherical resin particles expressed in Equation below is 2.0 or less.

[Equation]

$$(\text{Superficial index value})=(\text{Specific surface area actual measurement})/(\text{Specific surface area calculation})$$

$$(\text{Specific surface area calculation})=6\Sigma(n\times R^2)/\{\rho\times\Sigma(n\times R^3)\}$$

(Wherein, n=number of particles in a channel in a Coulter counter, R=channel particle size in the Coulter counter, ρ=toner density, number of channels: 16, division size: 0.1 intervals by log scale.)

(5) The emulsified cosmetic according to any of (1) to (4), wherein the spherical resin particles are an acrylic copolymer.

(6) The emulsified cosmetic according to any of (1) to (5), wherein the spherical resin particles are prepared by an emulsion polymerization aggregation method.

DETAILED DESCRIPTION OF THE INVENTION

As a result of attentive consideration of emulsified cosmetics superior in usability and a feel after application, and superior in secular stability, the present inventors have found it possible to create an emulsified cosmetic having superior characteristics and superior stability through a blending of resin particles of certain specific diameters and particle size distribution within a certain range and having hydroxyl groups on their surfaces.

The emulsified cosmetic in the present invention includes all cosmetics in which an oil phase comprising oil and fat content and an aqueous phase comprising aqueous components are stably dispersed, regardless of water-in-oil emulsification type or oil-in-water emulsification type. For example, such emulsified cosmetics would include basic skin cares such as creams, emulsions, massage creams, peel-off packs and washing packs, make-up cosmetics such as foundations (including foundations that are solid when formed but liquefy when taken up by a sponge), foundations and bases, lip colors, eye shadows and eyeliners, hair care cosmetics such as hair dyes and hair creams, and washing cosmetics such as shampoos, rinses and body soaps.

The cosmetic of the present invention has the following constitution.

The emulsified cosmetic comprises 0.1 to 25 wt % of aqueous moisturizing components; 2 to 80 wt % of oil solution components; and 0.1 to 30 wt % of spherical resin particles having hydrophilic groups on their surfaces and an average volume particle size of 2.0 µm to 20.0 µm.

Aqueous Moisturizing Components

The aqueous moisturizing components are not limited as long as they are for use in cosmetics, and include, for example, alcohols such as glycerin, 1,3-butylene glycol, dipropylene glycol and propylene glycol, water-soluble polymers such as hyaluronic acid and chondroitin sulfate, salts such as sodium lactate, sodium citrate, sodium glutamate, sodium 2-pyrrolidone carboxylate, sodium chloride, and magnesium chloride.

These components are present in an amount of 0.1 to 25 wt %. If below 0.1 wt %, it is not possible to have moisturizing effects, which might cause effects such as a dried skin. If 25 wt % is exceeded, stability of the emulsified cosmetic may be impaired.

Oily Components

The oily components are not limited as long as they are for use in cosmetics, and can include fats and oils, waxes, carbon hydrides, synthetic esters, fatty acids and higher alcohols. Specific examples could include fats and oils such as camellia oil, olive oil, jojoba oil, castor oil and mink oil, waxes such as carnauba, beeswax, lanoline and candelilla, carbon hydrides such as squalane, Vaseline, liquid paraffin, paraffin wax and microcrystalline wax, fatty acids such as stearic acid and oleic acid, higher alcohols such as cetanol, stearyl alcohol, oleyl alcohol and behenyl alcohol, esters such as cetylisooctanate, isopropyl myristate and glyceryl trioctanate, lanoline derivative, silicones, fluoric oil agents. One kind or a combination of two or more kinds of these oils can be used.

The blending amount of these oil solutions into the cosmetic is 2% to 80 wt %. When the oil solutions are below 2 wt %, it is difficult to perform emulsification because oily components are less than other components, and contrarily, when exceeding 80 wt %, fattiness, stickiness and glistening brought by the oil solutions are caused, which are not preferable for the cosmetics. The preferable blending amount is 10 to 60 wt %.

Spherical Resin Particles

Particle Size:

The resin particles contained in the cosmetic of the present invention have an average volume particle size of 2.0 µm to 20.0 µm, and more preferably 5.0 µm to 15.0 µm. If the particle size exceeds 20.0 µm, a sensation of a foreign body is caused when the resin particles are applied as a cosmetic, leading to inferior usability. If the particle size is below 2.0 µm, the viscosity of an oil layer is increased, reducing the effects of controlling stickiness.

Volume particle size distribution and shape factor SF1:

The volume particle size distribution GSDv of the spherical resin particles of the present invention is 1.3 or less, and the shape factor SF1 thereof is 100 to 140. In this range, the particle sizes of the resin particles blended into the cosmetic are uniform and particles close to a spherical form are blended, thereby enabling spreading during application and controlling stickiness after application.

When the volume particle size distribution GSDv of the spherical resin particles exceeds 1.3, the particle sizes are not uniform, such that, as a result, the smoothness and spread during use and the effects of refreshing feeling to be insufficient. As an index of the particle size distribution, it is possible to simply utilize the volume particle size distribution GSDv as indicated below or the number particle size distribution GSDp using D16 and D84 of a volume cumulative distribution.

[Equation]

Volume particle size distribution $GSDv=(\text{Volume } D84/\text{Volume } D16)^{0.5}$ Number particle size distribution $GSDp=(\text{Number } D84/\text{Number } D16)^{0.5}$ Furthermore, the shape factor SF1 is defined as follows:

[Equation]

$SF1=(ML^2/A) \times (\pi/4) \times 100$ where ML: Absolute maximum length of particle, A: Project area of particle, and these are digitalized mainly by having microscope images and scanning electronic microscope images analyzed by an image analyzing apparatus.

The smoothness desired in cosmetics depends greatly upon the fluidity of the particles. As the shape factor SF1 approaches 100, the particle is regarded as being close to the spherical form, and the particle exceeding 140 has a big difference between a maximum length and a minimum length. When the SF1 of the resin particles is in a range of 130 to 140, it is possible to feel the particles on the skin during use because resin corpuscles are humilis, which is preferable for such a cosmetic as the facial wash. On the other hand, when the SF1 is in a range of 110 to 130, the particle shape is close to the spherical form, and the fluidity on the skin surface improves, thereby enabling the spread during application in the case where the particles are blended into the make-up cosmetic, and uniform application onto the skin.

Superficial Index Value:

The resin corpuscles of the present invention have a superficial index value expressed in Equation below of 2.0 or less.

[Equation]

(Superficial index value)=(Specific surface area actual measurement)/(Specific surface area calculation)

(Specific surface area calculation)=$6\Sigma(n \times R^2)/\{\rho \times \Sigma(n \times R^3)\}$ (Wherein, n=number of particles in a channel in a Coulter counter, R channel particle size in the Coulter counter, ρ=toner density, number of channels: 16, division size: 0.1 intervals by log scale.)

From this it can be understood that the number of divisions is determined so as to divide into 16 channels at 0.1 intervals by log scale from 1.26 μm to 50.8 μm. Concretely, division has been made with 1.26 μm or more and below 1.59 μm in channel 1, 1.59 μm or more and below 2.00 μm in channel 2, and 2.00 μm or more and below 2.52 μm in channel 3, in a way that a log value of a numerical value on a left side will be (log 1.26=) 0.1, (log 1.59)=0.2, 0.3 . . . 1.6.

The resin surface becomes perfectly flat and smooth as the superficial index value approaches 1.0. If the superficial index value exceeds 1.3, the surfaces of each resin become rough, which decreases the usability when contained in the cosmetics and used.

The resin particles of the present invention are blended into the cosmetic by 0.1 to 30 wt %. When below 0.1%, good spread and a dry feeling are not demonstrated because of a too small blending amount, and when exceeding 30 wt %, stability of the emulsified cosmetics is damaged, and a gritty feel is caused. Further, to have the hydrophilic group signifies those that have a numerical value of an acid value or a hydroxyl value of 1.0 or more. Those of 2.0 or more are good in preparing the effects, and therefore preferably used.

Resin:

The resin of the present invention is a resin having a hydrophilic group on the surface. Polar groups as the hydrophilic group would include acid polar groups such as carboxyl group, sulfonic group, phosphoric group and formyl group; basic polar groups such as amino group; and neutral polar groups such as amide group, hydroxyl group and cyano group. These polar groups can be obtained by such methods wherein the polar group is introduced by a reaction to a copolymerization of monomers having the polar groups, condensation polymerization of low molecules having the polar groups, addition polymerization and a polymer.

The monomers or low molecules having the polar group are used preferably by 0.01 to 20% in the whole reactive materials, and more preferably by 0.1 to 10%. If the amount of the monomers having the polar group exceeds the above upper limit, hydrophilicity that is too high weakens the affinity for the oil phase, and if the above lower limit is not reached, the affinity for the aqueous phase is weakened, and conservation stability is deteriorated.

Among the monomers having the polar group, the monomers having the acid polar group would include, α,β-ethylenic unsaturated compounds having the carboxyl group and α,β-ethylenic unsaturated compounds having the sulfonic group, for example.

The α,β-ethylenic unsaturated compounds having the carboxyl group would include, for example, acrylic acid, methacrylic acid, fumaric acid, maleic acid, itaconic acid, cinnamic acid, monomethyl maleate, monobutyl maleate and monooctyl maleate. The α,β-ethylenic unsaturated compounds having the sulfonic group would include, for example, sulfonated ethylene, its Na salt, allylsulfosuccinic acid and octyl allylsulfosuccinate.

Among the monomers having the polar group, the monomers having the basic polar group would include, for example, carbon atom numbers 1 to 12 having an amino group, salt of amino group and quaternary ammonium group, preferably 2 to 8, and in particular, preferably ester (meth) acrylate of aliphatic alcohol of carbon atom number 2, vinyl compounds substituted with a heterocyclic group having N as a cyclic member and N, N-diallyl-alkylamine or its quaternary ammonium salt. Among these, ester (meth)acrylate of aliphatic alcohol having the amino group, salt of amino group and quaternary ammonium group is preferably used as a comonomer having basicity.

The ester (meth)acrylate of aliphatic alcohol having the amino group, salt of amino group and quaternary ammonium group would include, for example, dimethylaminoethylacrylate, dimethylaminoethylmethacrylate, diethylaminoethylacrylate, diethylaminoethylmethacrylate, quaternary salts of these, 3-dimethylaminophenylacrylate, 2-hydroxy-3-methacryloxypropyltrimethylammonium salt.

The vinyl compounds substituted with the heterocyclic group having N as the cyclic member would include, for example, vinylpyridine, vinylpyrrolidone, vinyl N-methylpyridiniumchloride and vinyl N-ethylpyridiniumchloride. The N,N-diallyl-alkylamine would include, for example, N,N-diallylmethylammoniumchloride, N,N-diallylethylammoniumchloride.

Among the monomers having the polar group, the monomers having the neutral polar group would include, for example, amide (meth)acrylate or amide (meth)acrylate which is monosubstituted or disubstituted with the alkyl group of carbon atom numbers 1 to 18 on optional N, ester (meth)acrylate having the hydroxyl group and, (meth)acrylic nitrile having the cyano group.

The amide (meth)acrylate or amide (meth)acrylate which is monosubstituted or disubstituted with the alkyl group of carbon atom numbers 1 to 18 on optional N would include, for example, acrylamide, N-butylacrylamide, N,N-dibutylacrylamide, piperidilacrylamide, methacrylamide, N-butylmethacrylamide, N,N-dimethylacrylamide and N-octadecileacrylamide.

The ester (meth)acrylate having the hydroxyl group would include, for example, 2-hydroxyethyl (meth)acrylate and 2-hydroxypropyl (meth)acrylate.

The low molecules having the carboxyl group used for the condensation polymerization or addition polymerization as the polar group would include aromatic dicarboxylic acids such as terephthalic acid, isophthalic acid, phthalic anhydride phthalate, benzenel.2.4 tricarboxylic acid, benzenel.2.5 tricarboxylic acid, naphthalene2.5.7 tricarboxylic acid and naphthalenel.2.4 tricarboxylic acid; aliphatic carboxylic acids such as oxalic acid, malonic acid, succinic acid, glutaric acid, adipic acid, hexahydro phthalic anhydride, itaconic acid, maleic acid, fumaric acid, mesaconic acid, citraconic acid, 1.2.4 butanetricarboxylic acid, hexanel.2.5 tricarboxylic acid, 1.3-dicarboxy-2-carboxymethylpropene, 1.3-dicarboxy-2-methyl-2-carboxymethylpropane, tetra (carboxymethyl) methane, octanel.2.7.8 tetracarboxylic acid and maleic anhydride; alicyclic carboxylic acids such as tetrahydrophthalic acid, hexahydrophthalic acid, methyltetrahydrophthalic acid, methylhexahydrophthalic acid, methylhymic acid, trialkyltetrahydrophthalic acid and methylcyclohexenedicarbon acid and their anhydrates.

The low molecules having the amino group used for the condensation polymerization or addition polymerization as the polar group would include chain aliphatic amines such as ethylenediamine, diethylenetriamine, triethylenetetramine, tetraethylenepentamine, dipropylenediamine, diethylaminopropylamine and hexamethylenediamine; cyclic amines such as menthenediamine, isophoronediamine, bis (4-amino-3-methyldincrohexyl) methane, diaminodincrohexylmethane, bis (aminomethyl) cyclohexane and N-aminoethylpiperazine; and aromatic amines such as methaphenylenediamine, diaminodiphenylmethane, diaminodiphenylsulfone and diaminodiethyldiphenylmethane.

The low molecules having the hydroxyl group used for the condensation polymerization or addition polymerization as the polar group would include a water, aliphatic diols such as ethyleneglycol, propyleneglycol, hexyleneglycol, glycerin, trimethylenepropane, hexanetriol, triethanolamine, diglycerin, pentaerythritol and methylglycoside; aliphatic hydroxylphenyl substitutes such as 1,1-bis (4-hydroxylphenyl) methane and 2,2-bis (4-hydroxylphenyl) propane; etherified bisphenol compounds such as polyoxyethylene (2,2) -2,2-bis (4-hydroxylphenyl) propane, polyoxyethylene (4,0) -2,2-bis (4-hydroxylphenyl) propane, and polyoxyethylene (2,2) -2,2-bis (4-hydroxylphenyl) propane.

As other low molecules having the polar group used for the condensation polymerization or addition polymerization, it is also possible to use compounds in which the sulfo group, phosphate group, formyl group or the like are combined with the above compounds of various kinds.

The carboxyl group is an especially preferable hydrophilic group. The hydrophilic group may be composed of one of the polar groups noted above or a combination of two or more of those, or the composition may be a combination of functional groups having different polarities (e.g., betaine structure). With these functional groups, the resin surface that originally has lipophilicity will have hydrophilicity, and it is possible to prevent detachment or aggregation of the resin in emulsified cosmetics that have both the aqueous phase containing the moisturizing components and the oil phase such as the oil solution, thereby maintaining the uniformity of the cosmetics.

Furthermore, the resins used for the resin corpuscles of the present invention are not specifically limited as long as they are resins that can be combined with the resins having the hydrophilic groups mentioned above. Concrete examples include styrenes such as styrene, parachlorostyrene and α-methylstyrene; acrylic monomers such as methyl acrylate, ethyl acrylate, n-propyl acrylate, lauryl acrylate and 2-ethylhexyl acrylate; methacrylic monomers such as methyl methacrylate, ethyl methacrylate, n-propyl methacrylate, lauryl methacrylate and 2-etylhexyl methacrylate; ethylene unsaturated acid monomers such as acrylic acids, methacrylic acids and sodium sthyrenesulfonate; vinylnitriles such as acrylonitrile and methacrylonitrile; vinylethers such as vinylmethylether and vinylisobutylether; vinylketones such as vinylmethylketone, vinylethylketone and vinylisopropenylketone; homopolymers such as monomers such as olefines such as ethylene, propylene and butadiene, copolymers combining two or more kinds of these monomers, or mixtures of these, and moreover, epoxy resin, polyester resin, polyurethane resin, polyamide resin, cellulose resin, polyether resin and the like, nonvinyl condensation resin, or mixtures of these and the vinyl resins mentioned above, and graft polymers obtained by polymerizing vinyl monomers under the condition in which these coexist. Among these, acrylic copolymers are preferably used as the resins blended to give a characteristic for use in skin external use compositions. Most preferably, styrene-acrylate copolymers are used.

The spherical resin particles of the present invention may have a small amount of cross-linking structure. In such a case, the content of a cross-liking agent is 0.01 to 5%, more preferably 0.1 to 2%, for the resin. As described further below, the shape is stabilized because the small amount of cross-linking structure is applied, with the soft physical properties resulting from the glass-transition temperature and molecular weight, thereby providing more effects of preventing aggregation. If the cross-liking agent is below this range, the shape of the resin is likely to be unstable, and, if this range is exceeded, the soft physical properties are decreased.

As the cross-liking agent, those that are suitable in relation to the above resins may be properly selected. Among these, boric compounds are preferable in terms of a quick cross-linking response. For example, borax, boric acid, borate salt (e.g., orthoboric salt), $InBO_3$, $ScBO_3$, $YBO_3$, $LaBO_3$, $Mg_3(BO_3)_2$, $Co_3(BO_3)_2$, diboric acid (e.g., $Mg_2B_2O_5$, $CO_2B_2O_5$), methaboric acid (e.g., $LiBO_2$, $Ca(BO_2)_2$, $NaBO_2$, $KBO_2$), tetraboric acid (e.g., $Na_2B_4O_7.10H_2O$), pentaboric acid (e.g., $KB_5O_3.4H_2O$, $Ca_2B_6O_{11}$, $7H_2O$, $CsB_5O_5$); aldehyde compounds such as formaldehyde, glyoxal, melamin.formaldehyde (e.g., methylolmelamin, methylolmelamin alkylate) and glutaraldehyde; ketonic compounds such as diacetyl and cyclopentanedione; active halogenated compounds such as bis (2-chloroethyl urea) -2-hydroxy-4,6-dichloro-1,3,5-triazine, and 2,4-dichloro-6-S-triazine-sodium salt; active vinyl compounds such as divinylsulfonic acid, 1,3-vinylsulfonyl-2-propanol, N,N'-ethylenebis (vinylsulfonylacetamido), 1,3,5-triacryloyl-hexahydro-S-triazine; N-methylol compounds such as dimethylol urea and methyloldimethylhydantoin; resole resin; isocyanate compounds such as polyisocyanate and 1,6-hexamethylenedisocyanate; an aziridine compound disclosed in U.S. Pat. No. 3,017,280 and No. 2,983,611; a carboxyimide compound disclosed in U.S. Pat. No. 3,100,704; epoxy compounds such as epoxy resin and glyceroltriglycidylether; ethyleneimino compounds such as 1,6-hexamethylene-N,N'-bisethylene urea; carboxyaldehyde halide compounds such as mucochlor acid and mocophenoxychlor acid; dioxane compounds such as 2,3-dihydroxydioxane; chrome alum, aluminum potassium alum, zirconium sulfate and chrome acid. It should appreciated that the cross-liking agent may be just one type or may be a combination of two or more types.

A solution of the cross-liking agent is composed by dissolving the cross-liking agent into water and/or an organic solvent. Water is generally used as the solvent that constitutes the cross-liking agent solution, which may be a water-based mixed solvent that contains the organic solvent miscible with the water. As the organic solvent, those that allow the cross-liking agent to be dissolved into may arbitrarily be used, including, for example, alcohols such as methanol, ethanol, isopropyl alcohol and glycerin; ketones such as acetone and methylethylketone, esters such as methyl acetate and ethyl acetate; aromatic solvent such as toluene; ether such as tetrahydrofuran, and carbon halide solvent such as dichloromethane.

Glass-Transition Temperature:

The glass-transition temperature of the spherical resin particles of the present invention is 10 to 100° C., preferably 10 to 90° C., and most preferably 40 to 80° C. When the glass-transition temperature is below 10° C., the cosmetic is too soft. On the other hand, when the glass-transition temperature exceeds 100° C., the adhesive feeling of the cosmetic onto the skin is decreased, and a rough feeling is caused during use.

Number Average Molecular Weight (Mn):

In the resin particles of the present invention, the number average molecular weight is 5000 to 100,000, and preferably 5000 to 20,000. When the resin number average molecular weight is below 5000, the cosmetic is too soft. On the other hand, when the number average molecular weight exceeds 100,000, the adhesive feeling of the cosmetic onto the skin is decreased and the cosmetic feels rough during use. That is, when the glass-transition temperature and the number average molecular weight exceed the ranges mentioned above, the resin becomes too soft or too hard, affecting usability, storability, and the like.

Resin Particle Preparation Method:

Methods of obtaining the spherical resin particles of the present invention would include an emulsion polymerization aggregation method, a suspension polymerization method and a dispersion polymerization method. Among these, the emulsion polymerization aggregation method is preferably used. When the cross-liking agent is added, it is preferable that the agent be added at the time of polymerizing the resin.

In the emulsion polymerization aggregation method, an ionic surfactant having a polarity reverse to that of the resin dispersion liquid based on the ionic surfactant is mixed, and heteroaggregation is caused to form the aggregated particles of the desired resin particle size, and then the aggregation is fused and coalesced by being heated to the glass-transition temperature of the resin or more before washed and dried. This preparing method makes it possible to control toner shape from an indefinite form to a spherical shape by the selection of heating temperature conditions.

Normally, the aggregating and coalescing process in the emulsion polymerization aggregation method is performed by collectively mixing and aggregating, so that it is possible to unite the aggregation that is in a uniform mixed state, and normally the composition of the aggregation is uniform from the surface to the inside.

Furthermore, the spherical resin particles of the present invention are desirably applied to alkali cleaning or acid cleaning as cleaning, after a particle forming process for fusing and coalescing the aggregation in the emulsion polymerization aggregation method mentioned above. Especially, when the hydrophilic group is an acidic group, the alkali cleaning is preferably used, and when the hydrophilic group is a basic group, the acid cleaning is preferably used. By undergoing the cleaning process, although a physicality index of the resin surface mentioned above remains the same state (i.e., the index mentioned above has no influence on a numerical value range), micro etching surfaces are formed which have very shallow unevenness observed by a high resolution scanning electrical microscope. As a result, a friction force against other minute cosmetic components is improved, and those other components become easy to stick to the resin surface, which inhibits the aggregation from occurring after mixture, thereby making it possible to maintain dispersibility. Meanwhile, adhesive strength is low because of the very shallow unevenness, so that the cosmetic is easily separated when applied, thus not impairing the functionality of the components and the spreadability of the resin. The washing agent used for the alkali cleaning is not limited as long as it is, for example, a water-based solution having alkalinity. Exmaples include sodium hydroxide water solution, potassium hydroxide water solution, ammonia water solution and sodium carbonate. Especially, sodium hydroxide is preferable. The washing agent used for the acid cleaning would include nitric acid, sulfuric acid, hydrochloric acid, and the like.

The feel of the cosmetic and characteristic deterioration are greatly concerned with the matter of coarse particle ratio. In the case of the preparing method of the present invention, the particles indicating the favorable particle size distribution GSD tend to be obtained easily, compared with normal methods, however, it is generally difficult to manage a volume particle ratio beyond 20 μm with the GSD. In the spherical resin particles of the present invention, if the ratio of the particles whose volume particle size is beyond 25 μm is 3% or more, smooth spreading on the skin would not be demonstrated and uniformity during application would be lost.

Other Characteristics of Resin Particles:

The smoothness at the time of application to the skin is obtained when the fluidity of the particles is high. As to a compression ratio, laxation apparent gravity and solidity apparent gravity are measured by using "Powder Tester" (registered trademark) manufactured by Hosokawamicron Corporation, and a ratio between the solidity apparent gravity and a difference between the solidity apparent gravity and the laxation apparent gravity is determined to be the compression ratio. A compression ratio of 0.6 or less indicates that the particles are in the normal state and have superior fluidity. When this range is exceeded, smooth application to the skin may not be possible.

The percentage of water content in the resin also greatly influences its fluidity. When the particles contain much water, a dry feeling is reduced, and the spreadability during application is hampered. Fluidity can be improved by blending the resin particles having a percentage of water content of 3% or less into compositions for external use. The percentage of water content can be measured by an appropriate publicly known method, and is not limited.

An acid value has an influence on the adhesion and aggregation between the resin particles and other substances as well as on sebum resistance of the resin and adsorbability into the skin. When a resin having an acid value ranging from 1.0 mg/KOH/g to 50 mg/KOH/g is blended into the cosmetic, the cosmetic can be washed off with ordinary soap or facial wash. Further, in the acid value range mentioned above, if other corpuscles are stuck onto the surface of the present resin particles, adhesion strength appropriate for the cosmetic or wash will be provided, and moreover the resin particles do not aggregate each other.

A hydroxyl value has an influence on the adhesion and aggregation between the resin particles and other substances as well as on sebum resistance of the resin, adsorbability into the skin and the affinity for water. When a resin having a hydroxyl value ranging from 1.0 mg/KOH/g to 50 mg/KOH/g is blended into the cosmetic, the cosmetic can be washed out with ordinary soap or facial wash. Further, in the hydroxyl value range mentioned above, if other corpuscles are stuck onto the surface of the present resin particles, adhesion strength appropriate for the cosmetic or wash will be provided, and, moreover, the resin particles do not aggregate with each other.

The resin particles used for the cosmetic of the present invention may contain other corpuscles. When the other corpuscles are contained in such a way, it is possible to have more of the effects of preventing re-aggregation compared with the case where the corpuscles are blended as they are, and it is possible to draw a function derived from the corpuscles while maintaining the usability based on the characteristics possessed by the resin particles in which the corpuscles are contained. The size of the corpuscles contained in the resin particles depends upon their content, but the size of the resin particles containing the corpuscles is preferably 3 μm or less. If this range is exceeded, the adhesion strength onto the particle surface is weakened. The combination of containing particles and contained corpuscles especially preferable is when (diameter of containing particles)/(diameter of contained corpuscles) is 2 or more.

Methods of containing the corpuscles in the resin particles would include a method of having the corpuscles precipitated onto the resin surface, a method of having the corpuscles contained inside the resin, and a method of attaching the corpuscles outside the resin.

As the method of precipitating onto the surface of the resin particles, for example, after parent aggregated particles are made with the resin particles in a first step of the aggregation process of the emulsion polymerization aggregation method, the dispersion liquid of the other corpuscles (e.g., functional corpuscles) is used in a second step of the aggregation process, thereby forming an encapsulated structure by the other corpuscles after coalescing. In another way, by reducing the resin in which the other corpuscles are ion-exchanged or coordinated to a polar group of the resin in a state of ions, metallic micro corpuscles can be precipitated onto the resin.

Furthermore, at the time of creating the parent aggregated particles in the first step of the emulsion polymerization aggregation method, if the other corpuscles are dispersed with the resin particles, it is possible to form the resin particles having a capsulation structure that contain the other corpuscles inside. In the case of external attachment, it is possible to apply a method of affixing the other corpuscles onto the surface in a dry manner with a mixer such as a V blender or a Henschel mixer after the resin particles are dried, and a method of, after the other corpuscles are dispersed into a liquid, having the other corpuscles added to compositions of an embrocation in a slurry state and dried and stuck onto the surface; it is also possible to dry while the slurry is sprayed over dry fine particles.

Other corpuscles to be contained in the resin particles are not specifically limited. Those that are generally blended into the cosmetics, such as pigments, an ultraviolet masking agent, an ultraviolet absorbent, an infrared masking agent, an antibacterial agent, and others may be used as preferable and appropriate.

Components blended into the emulsified cosmetic of the present invention other than the materials already mentioned are selected in accordance with intentioned use of the cosmetics, and are not limited. Examples of possible components include water, alcohols, a non-ionic surfactant, an anionic surfactant, a cationic surfactant, an ampholytic surfactant, an emulsifier, a binder, a dispersant, powders except for the spherical resin mentioned above, pigments, coloring matters, the ultraviolet masking agent, anhidrotics, the ultraviolet absorbent, an astringent agent, a coating agent, a moisturizing agent, cleaning components, medicinal components of various kinds, a pH adjuster, a thickener, an antioxidizing agent, a bactericide, an antibacterial agent, an antiseptic agent, beauty components, and perfumes. Further, the powder may be blended after silicone treatment, metallic soap treatment, fatty acid treatment, surfactant treatment, or treatment with acid, alkali or inorganic salts, or complex treatment using any of these.

Preparation methods of the cosmetic are not specifically limited, and methods generally employed can be adopted. Generally, an aqueous phase portion is confected with a phase in which hydrophilic components such as a moisturizing agent are added to purified water, and an oil phase portion is confected with a phase in which lipophilic components are added to oil solution components an oil phase portion. These are each heated to 60° C. or more, gradually mixed and emulsified. After the emulsification, they are cooled down and filled into containers. It is appreciated that the emulsified cosmetic of the present invention can be prepared whether an emulsion made by mixing and confecting the oil phase and the aqueous phase is of water-in-oil type (W/O type) or oil-in-water type (O/w type).

EXAMPLE

Next, the present invention will be described in fuller detail referring to Examples and Comparative Examples, however, the present invention is not limited to those Examples.

The resin particles were prepared in the following compositions.

Confection of Resin Dispersion Liquids 1 and 2

TABLE 1

| Composition | Resin dispersion liquid 1 (g) |
|---|---|
| Styrene | 540 |
| n-butylacrylate | 60 |
| Acrylic acid | 12 |
| DDT: dodecanethiol | 12 |

TABLE 2

| Composition | Resin dispersion liquid 2 (g) |
|---|---|
| Styrene | 360 |
| n-butylacrylate | 240 |
| BQA: 2-hydroxypropyl-N,N,N-trimethylammoniumchlorideacrylate | 30 |
| DDT: dodecanethiol | 12 |

With the compositions of the resin dispersion liquids 1, 2 shown in Tables 1, 2, one made by mixing and dissolving the components of the resin dispersion liquid is dispersed and emulsified in a flask into one made by dissolving 13 g of the anionic surfactant "NEOGEN R" (manufactured by Daiichikogyo Seiyaku Co., Ltd.: sodium dodesylbenzenesulfonate) into 555 g of deionized water, and mixed slowly for ten minutes, while adding 42.8 g of deionized water in which 9 g of ammonium persulfate was dissolved, and then applied to nitrogen substitution in the flask. After this, the content was heated to 70° C. in an oil bath while being stirred in the flask, and the emulsification polymerization was continued for six hours, thereby obtaining the resin corpuscle dispersion liquids.

Confection of Aggregated Particles 1

Using the prepared resin dispersion liquid 1, resin particles were prepared with the following composition.

[Table 3]
Resin corpuscle dispersion liquid 1: 520 g
Resin corpuscle dispersion liquid 1 (for addition): 200 g
Polychlorinated aluminum 10 wt % water solution (manufactured by Asadakagaku Corporation): 4.2 g
0.02 M nitric acid: 38 g Confection of Aggregated Particles 2

Using the prepared resin dispersion liquid 2, resin particles were prepared with the following composition.

[Table 4]
Resin corpuscle dispersion liquid 2: 520 g
Resin corpuscle dispersion liquid 2 (for addition): 200 g
Polychlorinated aluminum 10 wt % water solution (manufactured by Asadakagaku Corporation): 4.2 g
0.02 M nitric acid: 38 g Preparation of Manufacture Examples 1 to 3:

All of the components of the resin particles, except for the resin particle dispersion liquid (for addition), were put into a round stainless flask to be sufficiently mixed and dispersed with a homogenizer (manufactured by LKA Corporation, Ultra tarax T50), before they were heated to 60° C. while being stirred in the flask in the heating oil bath. After holding for 30 minutes at 60° C., 200 g of the resin dispersion liquid 1 was gently added, and the temperature of the heating oil bath was further raised. That temperature was maintained for the fixed periods of time indicated in Table below, thereby obtaining aggregated particles.

Subsequently, 1N sodium hydroxide solution is added to the aggregated particles cleaned with deionized water, and the pH is adjusted to about 6.0. Then, the stainless flask is hermetically sealed, and stirring was continued with a magnetic seal heating up to 96° C. The pH was adjusted to about 3.0 with 0.3 N nitric acid and maintained for about seven hours, such that the aggregated particles were fused. Then, the volume average particle size ($D_{SO}$) of the fused particles is measured with a Coulter counter (manufactured by Nikkaki Corporation, TAII). 1N sodium hydroxide solution was added to the dispersion liquid of the fused particles, and the pH was adjusted to about 10.0, and in that state those were stirred for 30 minutes before filtered and dispersed again into the purified water. After about 20 minutes of stirring and sufficient cleaning, freezing, and drying were performed, thereby obtaining the resin particles of the examples.

dine were added. A cooler is set to the Erlenmeyer flask, and a reaction was allowed to continue for 90 minutes at 90 to 100° C. 3 ml of distilled water was added from an upper part of the cooler, adequately shaken, and left for 10 minutes. After leaving and cooling, the cooler and the flask mouth were cleaned with a small amount of acetone from an upper opening of the cooler, 50 ml of THF was added with a graduated cylinder, and then titration was conducted with a 2 N KOH-THF solution.

[Equation]

$$\text{Hydroxyl value (mgKOH/g)} = ((B-S) \times f \times 112.2)/W$$

As to Manufacture Example 4, the resin particles were prepared in the same manner as in the preparing method of Manufacture Examples 1 to 3 except that the cleaning with deionized water was not applied.

As to Manufacture Examples 5 and 6, the resin particles were prepared in the same manner as in the preparing method of Manufacture Examples 1 to 3 except that the alkali clean-

TABLE 5

| | ME 1 | ME 2 | ME 3 | ME 4 | ME 5 | ME 6 | ME 7 | ME 8 |
|---|---|---|---|---|---|---|---|---|
| Resin dispersion liquid | 1 | 1 | 1 | 1 | 1 | 1 | 2 | — |
| Presence of hydrophilic group | Yes | Yes | Yes | Yes | Yes | Yes | Yes | No |
| 60° C. aggregating time (minute) | 30 | 30 | 30 | 30 | 30 | 5 | 30 | — |
| Conglobation time (minute) | 9 | 7 | 4 | 7 | 7 | 2.5 | 9 | — |
| pH cleaning | Yes | Yes | Yes | Yes | No | No | Yes | — |
| Pure cleaning | Yes | Yes | Yes | No | No | No | Yes | — |
| Average volume particle size (μm) | 6.6 | 6.7 | 6.8 | 6.5 | 6.7 | 6.6 | 6.3 | 8.2 |
| Average volume particle size distribution GSDv | 1.22 | 1.24 | 1.24 | 1.20 | 1.24 | 1.33 | 1.28 | 1.47 |
| Shape factor SF1 | 117 | 126 | 130 | 112 | 126 | 141 | 122 | 125 |
| Superficial index value | 1.37 | 1.46 | 1.39 | 2.08 | 2.10 | 2.11 | 1.51 | 1.23 |
| Glass-transition temperature (° C.) | 71 | 71 | 71 | 71 | 71 | 71 | 40 | 126 |
| Number average molecular weight Mn | $1.1 \times 10^4$ | $1.1 \times 10^4$ | $1.1 \times 10^4$ | $1.1 \times 10^4$ | $1.1 \times 10^4$ | $1.1 \times 10^4$ | $8.9 \times 10^3$ | $5.0 \times 10^3$ |
| Acid value (mg/KOH/g) | 5 | 5 | 5 | 5 | 5 | 5 | 1.0 | 0.5 |
| Hydroxyl value (mg/KOH/g) | 0.5 | 0.5 | 0.5 | 0.5 | 0.5 | 0.5 | 7 | 0.5 |
| Compression ratio | 0.48 | 0.51 | 0.56 | 0.47 | 0.47 | 0.63 | 0.54 | 0.60 |

ME - Manufacture Example
*A number average molecular weight was measured with a molecular weight measuring instrument (manufactured by Tosoh Corporation, HLC-8120). The glass-transition temperature was measured with Differential Scanning Calorimeter (manufactured by Shimadzu Corporation, DSC-50), at a programming rate of 10° C. /minute.
*As to the compression ratio, laxation apparent gravity X and solidity apparent gravity Y were measured with Powder Tester (manufactured by Hosokawamicron Corporation), and the calculation is performed by substituting the measured X, Y for the Equation below.

The acid value and hydroxyl value were measured in conformity with JIS K 0070. As to the acid value, the resin powder was accurately scaled, and a specimen was placed a 300 (ml) beaker, and then dissolved in 150 (ml) of a mixture liquid of toluene/ethanol (4/1) added to the mixture. Potentiometric titration was applied using a 0.1 normality (N) KOH methanol solution. At the same time, measurements were taken, and the acid value is found by the following Equation.

[Equation]

$$\text{Acid value (mgKOH/g)} = ((S-B) \times f \times 5.61)/W$$

where W is the weight (g) of the accurately scaled resin powder, S is the used amount (ml) of KOH, B is the used amount (ml) of KOH in the measurement in the blanks, and f is a factor of OH.

As to the hydroxyl value, 6 g of a specimen was accurately scaled with a 200 ml Erlenmeyer flask, and 5 ml of a mixed solution of acetic anhydride/pyridine=¼ and 25 ml of pyriing or acid cleaning, and purified water cleaning were not applied. As to Manufacture Example 7, the aggregated particles were fused in the same manner except that in the preparing method of Manufacture Examples 1 to 3, with the resin particles dispersion liquid 2, after cleaning the aggregated particles with deionized water, the pH was adjusted to about 4.0 using 0.3 N nitric acid and the stainless flask was hermetically sealed, stirring was continued with the magnetic seal heating up to 96° C., and then 1N sodium hydroxide solution is added and the pH is adjusted to about 8.0, which was maintained for seven hours to fuse the aggregated particles. Subsequently, 0.3 N nitric acid was added to the dispersion liquid of the fused particles, and the pH was adjusted to about 3.0, and in that state the dispersion liquid was stirred for 30 minutes before being filtered and dispersed again into the purified water. After about 20 minutes of stirring and sufficient cleaning, freezing and drying were performed, thereby obtaining the resin particles. It should be noted that Manufacture Example 8 uses commercially available spherical polymethylmethacrylate resin.

The following measurements were applied to the styrene-butylacrylate resin particles obtained as described. The average volume particle size ($D_{50}$) and the volume particle size distribution GSDv, and the ratio of the particles whose volume particle size is 20 μm or more were measured with Laser Scattering Particle Size Distribution Analyzer (manufactured by Horiba, Ltd., LA-700), and the shape factor SF1 was measured with LUZEX image analyzer (manufactured by Nireco Corporation, LUZEXIII). The superficial index value was calculated in accordance with the following Equations.

[Equation]

(Superficial index value)=(Specific surface area actual measurement)/(Specific surface area calculation)

(Specific surface area calculation)=$6\Sigma(n \times R^2)/\{\rho \times \Sigma(n \times R^3)\}$ (Wherein, n=number of particles in a channel in the Coulter counter, R=channel particle size in the Coulter counter, ρ=toner density, number of channels: 16, division size: 0.1 intervals by log scale.)

Preparation of W/O Emulsion:

The materials (10) and (11) were mixed in advance with a blender to create a powder portion. The materials (1) to (8) were heated and dissolved at 80° C. to produce a substance in the oil phase. The aqueous phase produced by heating the materials (12) to (14) was added to the oil phase little by little, and adequately stirred with the homomixer. While stirring and cooling, the powder portion was added at about 5° C., and the stirring was further continued, whereby the emulsion was prepared.

The emulsions prepared as described were applied to the skins of a panel of 20 men and women to conduct a sensory test. Evaluation standards in this test were set in the following manner concerning the spread during application and stickiness after application, and their average values are indicated in Table 6.

(Evaluation Standards on Spread)
Very good . . . 5
Good . . . 4
Normal . . . 3
Bad . . . 2
Very bad . . . 1

(Evaluation Standards on whether to Feel Stickiness)
Do not feel at all . . . 5
Hardly feel . . . 4
Feel to some degree . . . 3
Feel a little . . . 2
Feel . . . 1

(Standards on Cosmetic Stability)
The prepared cosmetics were left in an incubator at 40° C. for three months to observe any change in appearance, and evaluations were made by the standards shown below.
◎: No change
○: Slight change is recognized
Δ: Obvious change is recognized
x: Significant change is recognized Preparation of O/W Type Moisturizing Cream:

The materials (8) and (9) were premixed in a blender to create a powder portion. The materials (1) to (7) were heated and dissolved at 80° C. to produce the oil phase. The aqueous phase produced by heating the materials (10) to (12) at 80° C. was added to the oil phase little by little to be preliminarily emulsified. Those were then stirred with the homomixer, and, while being stirred, were cooled wile a powder portion was added at about 50° C. After further cooling while stirring, the cream was prepared.

TABLE 6

|  | Ex 1 | Ex 2 | Ex 3 | Ex 4 | Ex 5 | Ex 6 | Ex 7 | CEx 1 | CEx 2 |
|---|---|---|---|---|---|---|---|---|---|
| (1) Cetanol | 2 | 2 | 2 | 2 | 2 | 2 | 2 | 2 | 2 |
| (2) Beeswax | 1.5 | 1.5 | 1.5 | 1.5 | 1.5 | 1.5 | 1.5 | 1.5 | 1.5 |
| (3) Lanoline | 2 | 2 | 2 | 2 | 2 | 2 | 2 | 2 | 2 |
| (4) Isopropyl myristate | 3 | 3 | 3 | 3 | 3 | 3 | 3 | 3 | 3 |
| (5) Silicon oil | 9 | 9 | 9 | 9 | 9 | 9 | 9 | 9 | 9 |
| (6) | 3 | 3 | 3 | 3 | 3 | 3 | 3 | 3 | 3 |
| (7) | 1 | 1 | 1 | 1 | 1 | 1 | 1 | 1 | 1 |
| (8) Glyceryl stearate | 1.2 | 1.2 | 1.2 | 1.2 | 1.2 | 1.2 | 1.2 | 1.2 | 1.2 |
| (10) ME 1 | 10 | — | — | — | — | — | — | — | — |
| (10) ME 2 | — | 10 | — | — | — | — | — | — | — |
| (10) ME 3 | — | — | 10 | — | — | — | — | — | — |
| (10) ME 4 | — | — | — | 10 | — | — | — | — | — |
| (10) ME 5 | — | — | — | — | 10 | — | — | — | — |
| (10) ME 6 | — | — | — | — | — | 10 | — | — | — |
| (10) ME 7 | — | — | — | — | — | — | 10 | — | — |
| (10) ME 8 | — | — | — | — | — | — | — | — | 10 |
| (11) Titanium oxide | 1.5 | 1.5 | 1.5 | 1.5 | 1.5 | 1.5 | 1.5 | 1.5 | 1.5 |
| (12) 1,3-butylene glycol | 3 | 3 | 3 | 3 | 3 | 3 | 3 | 3 | 3 |
| (13) Glycerin | 2 | 2 | 2 | 2 | 2 | 2 | 2 | 2 | 2 |
| (14) Purified water | R | R | R | R | R | R | R | R | R |
| Spread during application | 4.9 | 4.7 | 4.4 | 3.8 | 2.5 | 2.4 | 4.2 | 2.7 | 2.2 |
| Stickiness after application | 4.7 | 4.6 | 4.4 | 4.1 | 3.4 | 3.1 | 4.4 | 2.0 | 2.9 |
| Stability of cosmetic | ◎ | ◎ | ◎ | ○ | Δ | ○ | Δ | x | x |

Ex - Example
CEx - Comparative example
ME - Manufacture example
R - Remaining amount
(6) Sorbitan sesquioleic acid ester
(7) Polyoxyethylenesorbitan monooleic acid ester

TABLE 7

|  | Ex 8 | Ex 9 | Ex 10 | Ex 11 | Ex 12 | CEx 3 | CEx 4 |
|---|---|---|---|---|---|---|---|
| (1) Cetanol | 3 | 3 | 3 | 3 | 3 | 3 | 3 |
| (2) Beeswax | 3 | 3 | 3 | 3 | 3 | 3 | 3 |
| (3) Squalane | 5 | 5 | 5 | 5 | 5 | 5 | 5 |
| (4) Vaseline | 2 | 2 | 2 | 2 | 2 | 2 | 2 |
| (5) Silicon oil | 10 | 10 | 10 | 10 | 10 | 10 | 10 |
| (6) Sorbitan sesquioleic acid ester | 1.5 | 1.5 | 1.5 | 1.5 | 1.5 | 1.5 | 1.5 |
| (7) Glyceryl stearate | 1.2 | 1.2 | 1.2 | 1.2 | 1.2 | 1.2 | 1.2 |
| (8) ME 1 | 10 | — | — | — | — | — | — |
| (8) ME 2 | — | 10 | — | — | — | — | — |
| (8) ME 3 | — | — | 10 | — | — | — | — |
| (8) ME 4 | — | — | — | 10 | — | — | — |
| (8) ME 6 | — | — | — | — | 10 | — | — |
| (8) ME 8 | — | — | — | — | — | 10 | — |
| (9) Titanium oxide | 1 | 1 | 1 | 1 | 1 | 1 | 1 |
| (10) 1,3-butylene glycol | 5 | 5 | 5 | 5 | 5 | 5 | 5 |
| (11) Glycerin | 4 | 4 | 4 | 4 | 4 | 4 | 4 |
| (12) Purified water | R | R | R | R | R | R | R |
| Spread during application | 4.9 | 4.8 | 4.7 | 4.1 | 3.6 | 3.0 | 3.0 |
| Stickiness after application | 4.6 | 4.4 | 4.2 | 3.9 | 3.8 | 3.1 | 1.8 |

Ex - Example
CEx - Comparative example
ME - Manufacture example
R - Remaining amount The creams prepared as described were applied to the skins of a panel of 20 men and women in all to conduct the sensory test. Evaluation standards in this test are common to the sensory test of the W/O emulsion described above. The results are indicated in Table 7 with their average values.

Preparation of O/W Type Peel-Off Pack:

The materials (1) to (3) were heated and dissolved at 70° C. to produce the oil phase. An oil phase made by wetting polyvinyl alcohol with denatured alcohol was added to and mixed with the aqueous phase produced by heating at 70° C. and stirring the materials (9) to (11). The aqueous phase was added to the oil phase little by little. The mixture was then adequately stirred with the homomixer, and then further cooled while being stirred. To this mixture, the powder portion in which (4), (7), and (8) are adequately mixed in advance was added at about 50° C., and those were cooled while the stirring was further continued, whereby the pack was prepared.

TABLE 8

|  | Ex 13 | Ex 14 | Ex 15 | Ex 16 | Ex 17 | CEx 5 | CEx 6 |
|---|---|---|---|---|---|---|---|
| (1) Cetanol | 1 | 1 | 1 | 1 | 1 | 1 | 1 |
| (2) Glycerin | 3 | 3 | 3 | 3 | 3 | 3 | 3 |
| (3) Glyceryl stearate | 1 | 1 | 1 | 1 | 1 | 1 | 1 |
| (4) ME 1 | 5 | — | — | — | — | — | — |
| (4) ME 2 | — | 5 | — | — | — | — | — |
| (4) ME 3 | — | — | 5 | — | — | — | — |
| (4) ME 4 | — | — | — | 5 | — | — | — |
| (4) ME 6 | — | — | — | — | 5 | — | — |
| (4) ME 8 | — | — | — | — | — | 5 | — |
| (5) Denatured alcohol | 10 | 10 | 10 | 10 | 10 | 10 | 10 |
| (6) Polyvinyl alcohol | 15 | 15 | 15 | 15 | 15 | 15 | 15 |
| (7) Titanium oxide | 5 | 5 | 5 | 5 | 5 | 5 | 5 |
| (8) Kaoline | 3 | 3 | 3 | 3 | 3 | 3 | 3 |
| (9) 1,3-butylene glycol | 2 | 2 | 2 | 2 | 2 | 2 | 2 |
| (10) Glycerin | 3 | 3 | 3 | 3 | 3 | 3 | 3 |
| (11) Purified water | R | R | R | R | R | R | R |
| Spread during application | 4.6 | 4.5 | 4.2 | 3.6 | 3.5 | 3.3 | 3.4 |

Ex - Example
CEx - Comparative example
ME - Manufacture example
R - Remaining amount The packs prepared as described were applied to the skins of a panel of 20 men and women to conduct the sensory test. Evaluation standards in this test were the same as in the sensory test of the W/O emulsion described above. The results are indicated in Table 8 with their average values.

Preparation of O/W Type Facial Cleansing Cream:

The materials (1) to (7) were heated and dissolved at 70° C. to produce the oil phase. The oil phase was added little by little to the aqueous phase made by heating the materials (9) to (13) at 70° C., to be preliminarily emulsified. The mixture is then stirred with the homomixer while cooling, and to this mixture the powder portion of (8) was added at about 50° C. After further cooling and stirring, a massage cream was prepared.

TABLE 9

| | Ex 18 | Ex 19 | Ex 20 | Ex 21 | Ex 22 | CEx 7 | CEx 8 |
|---|---|---|---|---|---|---|---|
| (1) Cetanol | 2 | 2 | 2 | 2 | 2 | 2 | 2 |
| (2) Beeswax | 3 | 3 | 3 | 3 | 3 | 3 | 3 |
| (3) Isopropyl myristate | 3 | 3 | 3 | 3 | 3 | 3 | 3 |
| (4) Olive oil | 5 | 5 | 5 | 5 | 5 | 5 | 5 |
| (5) Silicon oil | 20 | 20 | 20 | 20 | 20 | 20 | 20 |
| (6) Polysorbate | 2 | 2 | 2 | 2 | 2 | 2 | 2 |
| (7) Glyceryl stearate | 2.5 | 2.5 | 2.5 | 2.5 | 2.5 | 2.5 | 2.5 |
| (8) ME 1 | 8 | — | — | — | — | — | — |
| (8) ME 2 | — | 8 | — | — | — | — | — |
| (8) ME 3 | — | — | 8 | — | — | — | — |
| (8) ME 4 | — | — | — | 8 | — | — | — |
| (8) ME 6 | — | — | — | — | 8 | — | — |
| (8) ME 8 | — | — | — | — | — | 8 | — |
| (9) Potassium hydroxide | 1 | 1 | 1 | 1 | 1 | 1 | 1 |
| (10) 1,3-butylene glycol | 5 | 5 | 5 | 5 | 5 | 5 | 5 |
| (11) Glycerin | 4 | 4 | 4 | 4 | 4 | 4 | 4 |
| (12) Laurylbetaine | 8 | 8 | 8 | 8 | 8 | 8 | 8 |
| (13) Purified water | R | R | R | R | R | R | R |
| Spread during application | 4.9 | 4.8 | 4.8 | 3.9 | 3.7 | 3.4 | 4.0 |
| Massage effects | 4.3 | 4.6 | 4.8 | 4.1 | 4.1 | 4.0 | 2.1 |

Ex - Example
CEx - Comparative example
ME - Manufacture example
R - Remaining amount Facial cleansing creams prepared as described were applied to the skins of a panel of 20 men and women to conduct the sensory test. In this test, evaluation standards on the spread during application were the same as those in the W/O emulsion described above. As to the massage effects, the standards were set as shown below. The average values for the results of this sensory test are shown in Table 9.

(Evaluation Standards on Massage Effects)
Sufficient massage effects can be obtained . . . 5
Massage effects can be obtained . . . 4
Normal . . . 3
Massage effects are not felt very much . . . 2
Massage effects are not felt . . . 1

Preparation of Body Soap:

The materials except for (2) were added to a purified water phase heated at 70° C. While this mixture was uniformly mixed and cooled while being stirred, the mixture (2) was added at about 50° C. After further cooling and stirring, body soap was prepared as a result.

TABLE 10

| | Ex 23 | Ex 24 | Ex 25 | Ex 26 | Ex 27 | CEx 9 | CEx 10 |
|---|---|---|---|---|---|---|---|
| (1) Cocoanut oil fatty acid diethanolamide | 2 | 2 | 2 | 2 | 2 | 2 | 2 |
| (2) Squalane | 1.5 | 1.5 | 1.5 | 1.5 | 1.5 | 1.5 | 1.5 |
| (3) ME 1 | 5 | — | — | — | — | — | — |
| (3) ME 2 | — | 5 | — | — | — | — | — |
| (3) ME 3 | — | — | 5 | — | — | — | — |
| (3) ME 4 | — | — | — | 5 | — | — | — |
| (3) ME 6 | — | — | — | — | 5 | — | — |
| (3) ME 8 | — | — | — | — | — | 5 | — |
| (4) Polyethanolamine lauryl sulfate | 5 | 5 | 5 | 5 | 5 | 5 | 5 |
| (5) Laurylbetaine | 2 | 2 | 2 | 2 | 2 | 2 | 2 |
| (6) Sodium laurylpolyoxyethylene sulfate | 15 | 15 | 15 | 15 | 15 | 15 | 15 |
| (8) Purified water | R | R | R | R | R | R | R |
| Spread during application | 4.9 | 4.8 | 4.6 | 4.2 | 4.0 | 3.7 | 4.0 |
| Massage effects | 4.1 | 4.2 | 4.4 | 3.7 | 3.7 | 3.1 | 1.1 |
| Dry feeling after cleansing | 4.6 | 4.5 | 4.1 | 4.1 | 3.9 | 3.5 | 1.4 |
| Dry feeling after 30 minutes | 4.2 | 4.0 | 4.0 | 3.8 | 3.3 | 3.1 | 1.0 |

Ex - Example
CEx - Comparative example
ME - Manufacture example
R - Remaining amount The body soaps prepared as described were applied to the skins of a panel of 20 men and women to conduct the sensory test. In this test, evaluation standards on the spread during application are the same as those in the emulsion described above. For whether the dry feeling after washing hair was obtained immediately after washing and whether the dry feeling remained after 30 minutes, the standards were set as below. The average values for the results of this sensory test are indicated in Table 10.

(Evaluation Standards on Washing Effects)
Dry feeling can be obtained . . . 5
Dry feeling can be obtained a little . . . 4
Normal . . . 3
Dry feeling is not felt very much . . . 2
Dry feeling is not felt . . . 1

Preparation of Shampoo:

The materials other than (2) were added to the purified water phase heated at 70° C., and these were uniformly mixed and cooled while being stirred. To this mixture, mixture (2) was added at about 50° C., and then cooled while further stirred, thereby producing a shampoo.

TABLE 11

|  | Ex 28 | Ex 29 | Ex 30 | Ex 31 | Ex 32 | CEx 11 | CEx 12 |
|---|---|---|---|---|---|---|---|
| (1) Cocoanui oil fatty acid diethanol amide | 4 | 4 | 4 | 4 | 4 | 4 | 4 |
| (2) ME 1 | 2 | — | — | — | — | — | — |
| (2) ME 2 | — | 2 | — | — | — | — | — |
| (2) ME 3 | — | — | 2 | — | — | — | — |
| (2) ME 4 | — | — | — | 2 | — | — | — |
| (2) ME 6 | — | — | — | — | 2 | — | — |
| (2) ME 8 | — | — | — | — | — | 2 | — |
| (3) Potassium myristate | 10 | 10 | 10 | 10 | 10 | 10 | 10 |
| (4) Potassium laurate | 5 | 5 | 5 | 5 | 5 | 5 | 5 |
| (5) Polyoxyethylenelaurylether sodium sulfate | 10 | 10 | 10 | 10 | 10 | 10 | 10 |
| (6) Sodium laurylglutaminate | 7 | 7 | 7 | 7 | 7 | 7 | 7 |
| (7) Purified water | R | R | R | R | R | R | R |
| Spread during application | 4.9 | 4.7 | 4.6 | 4.2 | 3.8 | 3.7 | 4.0 |
| Dry feeling after washing | 4.3 | 4.2 | 3.9 | 3.7 | 3.5 | 3.1 | 1.1 |

Ex - Example
CEx - Comparative example
ME - Manufacture example
R - Remaining amount The shampoos prepared in this way were used to wash the hair of a panel of 20 men and women to conduct the sensory test. Evaluation standards in this test were the same as those used for the body soap described above. The average values for the results are indicated in Table 11.

Preparation of Rinse:

The materials (1) to (4) were heated and dissolved at 70° C. to produce the oil phase. The oil phase was added little by little to the aqueous phase made by heating the materials (6) to (8) at 70° C., to be preliminarily emulsified. This mixture was then stirred with the homomixer. After cooling while being stirred, mixture (5) was added at about 50° C. After further cooling and stirring, a rinse was prepared.

TABLE 12

|  | Ex 33 | Ex 34 | Ex 35 | Ex 36 | Ex 37 | CEx 13 | CEx 14 |
|---|---|---|---|---|---|---|---|
| (1) Cetanol | 1 | 1 | 1 | 1 | 1 | 1 | 1 |
| (2) Stearyl alcohol | 0.5 | 0.5 | 0.5 | 0.5 | 0.5 | 0.5 | 0.5 |
| (3) Polyoxyethylene-lanolinether | 1.0 | 1.0 | 1.0 | 1.0 | 1.0 | 1.0 | 1.0 |
| (4) Polysorbate | 0.5 | 0.5 | 0.5 | 0.5 | 0.5 | 0.5 | 0.5 |
| (5) ME 1 | 1.0 | — | — | — | — | — | — |
| (5) ME 2 | — | 1.0 | — | — | — | — | — |
| (5) ME 3 | — | — | 1.0 | — | — | — | — |
| (5) ME 4 | — | — | — | 1.0 | — | — | — |
| (5) ME 6 | — | — | — | — | 1.0 | — | — |
| (5) ME 8 | — | — | — | — | — | 1.0 | — |
| (6) Propylene glycol | 5.0 | 5.0 | 5.0 | 5.0 | 5.0 | 5.0 | 5.0 |
| (7) disteallyldimethyl-ammonium chloride | 2.0 | 2.0 | 2.0 | 2.0 | 2.0 | 2.0 | 2.0 |
| (8) Purified water | R | R | R | R | R | R | R |
| Spread of washing agent | 4.9 | 4.7 | 4.5 | 4.2 | 3.7 | 3.4 | 4.1 |
| Dry feeling after washing | 4.8 | 4.5 | 4.2 | 3.5 | 3.0 | 2.9 | 1.6 |

Ex - Example
CEx - Comparative example
ME - Manufacture example
R - Remaining amount The rinses prepared in this way were used by a panel of 20 men and women to conduct the sensory test. In this test, evaluation standards of spreading during application were the same as those used to evaluate body soap as described above. Table 12 shows the average values for the results of this sensory test.

Test Results:

From Tables 6 to 12, it is clear that the cosmetics in which the spherical resin particles of the present invention are blended are superior to comparative articles in spreadability and in control of stickiness after application. From to Table 9 and Table 10, it is clear that, because the effects are demonstrated when the shape is slightly uneven rather than spherical in the cosmetics such as the washes that are expected to provide a certain degree of massage effects and a refreshing feeling, the cosmetics of the present invention provide sufficient washing effect and spreadability. Further, according to Table 10, it is evident that the durability of the dry feeling after washing is felt more with uneven shaped particles than with those of spherical form.

The emulsified cosmetics of the present invention are prepared by blending an oil solution and a/moisturizing agent along with spherical resin particles. The spherical resin particles are characterized by a specific particle size and a narrow particle size distribution, and further by the blending of the resin particles having the hydrophilic group on the surface into the emulsified cosmetics. Additionally, because the surfaces of the spherical resin particles are very flat and smooth, the cosmetics in which this resin is blended show smooth spread during application and can reduce the stickiness after application. In cosmetics in which the spherical resin having unevenness are blended, it is possible to accomplish a feeling of particles such as massage effects and smooth spreading.

What is claimed is:

1. An emulsified cosmetic comprising:
   0.1 to 25 wt % of aqueous moisturizing components;
   30 to 80 wt % of oil solution components; and
   0.1 to 30 wt % of spherical resin particles prepared by an emulsion polymerization aggregation method, having hydrophilic groups from a surface to an inside of the particles and an average volume particle size of 2.0 µm to 20.0 µm, wherein the hydrophilic groups include acid polar groups, and a glass transition temperature of the spherical resin particles is in a range of 10 to 90° C., wherein the spherical resin particles are uniform in composition from the surface to the inside of the particles and are not hollow particles, wherein a volume particle size distribution GSDv of the spherical resin particles is 1.24 or less, wherein the spherical resin particles are formed from monomers having the hydrophilic groups, wherein the monomers having the hydrophilic groups comprise from 0.01 to 20% by mass of reactive materials for formation of the spherical resin particles, and wherein a superficial index value of the spherical resin particles expressed in an equation below is 2.0 or less, wherein
   (Superficial index value)=(Specific surface area actual measurement)/ (Specific surface area calculation),
   (Specific surface area calculation)=$6\Sigma(n \times R^2)/\{\rho \times \Sigma(n \times R^3)\}$, and
   (n=number of particles in a channel in a Coulter counter, R=channel particle size in the Coulter counter, ρ=toner density, number of channels: 16, division size: 0.1 intervals by log scale).

2. The emulsified cosmetic according to claim 1, wherein the spherical resin particles are made by applying alkali cleaning or acid cleaning to aggregation particles after resin polymerization.

3. The emulsified cosmetic according to claim 1, wherein a shape factor SF1 of the spherical resin particles is 100 to 140.

4. The emulsified cosmetic according to claim 1, wherein the spherical resin particles are an acrylic copolymer.

5. The emulsified cosmetic according to claim 1, containing 30 to 60 wt % of oil solution components.

6. The emulsified cosmetic according to claim 1, wherein the average volume particle size of the spherical resin particles is 5.0 µm to 15.0 µm.

7. The emulsified cosmetic according to claim 1, wherein a numerical value of an acid value or a hydroxyl value of the spherical resin particles is 1.0 to 50 mg/KOH/g.

8. The emulsified cosmetic according to claim 1, wherein a number average molecular weight of the spherical resin particles is in a range of 5000 to 100000.

9. The emulsified cosmetic according to claim 1, wherein a compression ratio of the spherical resin particles is 0.6 or less.

10. The emulsified cosmetic according to claim 1, wherein a percentage of water content of the spherical resin particles is 3% or less.

11. The emulsified cosmetic according to claim 1, wherein the aqueous moisturizing components are selected from glycerin, 1,3-butylene glycol, dipropylene glycol, propylene glycol, hyaluronic acid, chondroitin sulfate, sodium lactate, sodium citrate, sodium glutamate, 2-pyrrolidone, sodium carboxylate, sodium chloride, magnesium chloride and mixtures thereof.

12. The emulsified cosmetic according to claim 1, wherein the oil solution components are selected from fats and oils, waxes, carbon hydrides, synthetic esters, fatty acids, higher alcohols and mixtures thereof.

13. The emulsified cosmetic according to claim 1 for washing, wherein the SF1 of the spherical resin particles is in a range of 130 to 140.

14. The emulsified cosmetic according to claim 1 for makeup, wherein the SF1 of the spherical resin particles is in a range of 110 to 130.

15. The emulsified cosmetic according to claim 1, wherein the spherical resin particles comprise styrene-acrylic resin.

16. The emulsified cosmetic according to claim 1, wherein the spherical resin particles comprise vinyl resin.

* * * * *